US011911565B2

(12) United States Patent
Glen et al.

(10) Patent No.: US 11,911,565 B2
(45) Date of Patent: Feb. 27, 2024

(54) TWIST TO LOCK TRACHEOSTOMA HEAT AND MOISTURE EXCHANGER

(71) Applicant: Freudenberg Medical, LLC, Carpinteria, CA (US)

(72) Inventors: Kevin Alan Glen, Ventura, CA (US); Dimitrios Stroumpoulis, Santa Barbara, CA (US); Tejasvi Subramanya, Oxnard, CA (US)

(73) Assignee: Freudenberg Medical, LLC, Carpinteria, CA (US)

( * ) Notice: Subject to any disclaimer, the term of this patent is extended or adjusted under 35 U.S.C. 154(b) by 548 days.

(21) Appl. No.: 17/079,929

(22) Filed: Oct. 26, 2020

(65) Prior Publication Data

US 2022/0126053 A1 Apr. 28, 2022

(51) Int. Cl.
*A61M 16/10* (2006.01)
*A61M 16/04* (2006.01)

(52) U.S. Cl.
CPC ...... *A61M 16/1045* (2013.01); *A61M 16/047* (2013.01)

(58) Field of Classification Search
CPC .............. A61M 16/1045; A61M 16/20; A61M 16/201; A61M 16/047; A61M 16/0468; A61M 39/223; A61M 2039/224; A61M 2039/226; A61M 2039/229
See application file for complete search history.

(56) References Cited

U.S. PATENT DOCUMENTS

| | | | |
|---|---|---|---|
| 4,569,344 A * | 2/1986 | Palmer | A61M 1/7413 251/95 |
| 6,193,751 B1 * | 2/2001 | Singer | A61F 2/20 623/9 |
| 6,422,235 B1 | 7/2002 | Persson | |
| 6,772,758 B2 | 8/2004 | Lambert | |
| 8,887,718 B2 | 11/2014 | Shikani et al. | |
| 8,991,394 B2 | 3/2015 | Persson | |

(Continued)

FOREIGN PATENT DOCUMENTS

| | | |
|---|---|---|
| EP | 2367588 B1 | 3/2017 |
| WO | 0189318 A2 | 11/2001 |
| WO | 2015052121 A1 | 4/2015 |

OTHER PUBLICATIONS

International Search Report dated Feb. 8, 2022 (corresponding to PCT/US2021/056538).

*Primary Examiner* — Rachel T Sippel
*Assistant Examiner* — Douglas Y Sul
(74) *Attorney, Agent, or Firm* — Daniel J. Sepanik, Esq.; Harness, Dickey & Pierce, P.L.C.

(57) ABSTRACT

A twist to lock heat and moisture exchanging device includes a housing having a first opening that is adapted to open to a tracheostoma and a second opening that opens to ambient. A foam filter is disposed in the housing and a closure member is mounted to the housing and adapted to close a passage between the first opening and the second opening. A locking mechanism is engageable to prevent movement of the closure member to close the passage and disengageable to allow movement of the closure member to close the passage. The twist to lock tracheostoma heat and moisture exchanger allows a user to protect from accidental closure during activities when it would be preferred like sleeping and exercising.

7 Claims, 3 Drawing Sheets

(56) References Cited

U.S. PATENT DOCUMENTS

| | | |
|---|---|---|
| 2002/0156527 A1 | 10/2002 | Persson |
| 2006/0079827 A1* | 4/2006 | Jensen ................ A61M 1/3658 |
| | | 604/6.1 |
| 2007/0251523 A1 | 11/2007 | Landuyt |
| 2013/0192602 A1* | 8/2013 | Leibitzki ............. A61M 16/047 |
| | | 128/205.27 |
| 2015/0083119 A1 | 3/2015 | Persson |
| 2015/0238718 A1* | 8/2015 | Schnell .................... A61F 2/20 |
| | | 128/205.27 |
| 2018/0207382 A1* | 7/2018 | Kamradt ................. A61F 2/203 |
| 2020/0188620 A1* | 6/2020 | Markwardt ............. A61F 2/203 |
| 2022/0054781 A1* | 2/2022 | Worthington ............. A61F 2/20 |

* cited by examiner

TWIST TO LOCK TRACHEOSTOMA HEAT AND MOISTURE EXCHANGER

FIELD

The present disclosure relates to a heat and moisture exchanger and more particularly to a twist to lock heat and moisture exchanger.

BACKGROUND

This section provides background information related to the present disclosure which is not necessarily prior art.

Loss of nasal function as a result of laryngectomy can result in functional changes to tracheal bronchial mucosa and lung function. These changes are due to dry cool air replacing the warm humid air which was provided by the function of the nose and nasal passage. A total laryngectomy surgery also results in a decreased resistance which has effect on lung function. These functional changes can result in an increase in mucus production, an increase in coughing, and an increase in chest infections.

Daily use of a heat and moisture exchanger (hereinafter HME) reduces loss of heat and moisture from the tracheal and bronchial mucosa and lungs, and provides the lungs with increased resistance. This warm, humidified and filtered air helps keep the mucosa from drying out and the increased resistance keeps the alveoli of the lungs from collapsing resulting in better lung function.

SUMMARY

This section provides a general summary of the disclosure, and is not a comprehensive disclosure of its full scope or all of its features.

A twist to lock heat and moisture exchanging device includes a housing having a first opening that is adapted to open to a tracheostoma and a second opening that opens to ambient. A foam filter is disposed in a passage between the first opening and the second opening and a closure member is mounted to the housing and adapted to close the passage between the first opening and the second opening. A locking mechanism is engageable to prevent movement of the closure member to close the passage and disengageable to allow movement of the closure member to close the passage. The twist to lock tracheostoma heat and moisture exchanger allows a user to protect from accidental closure during activities when it would be preferred like sleeping and exercising.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
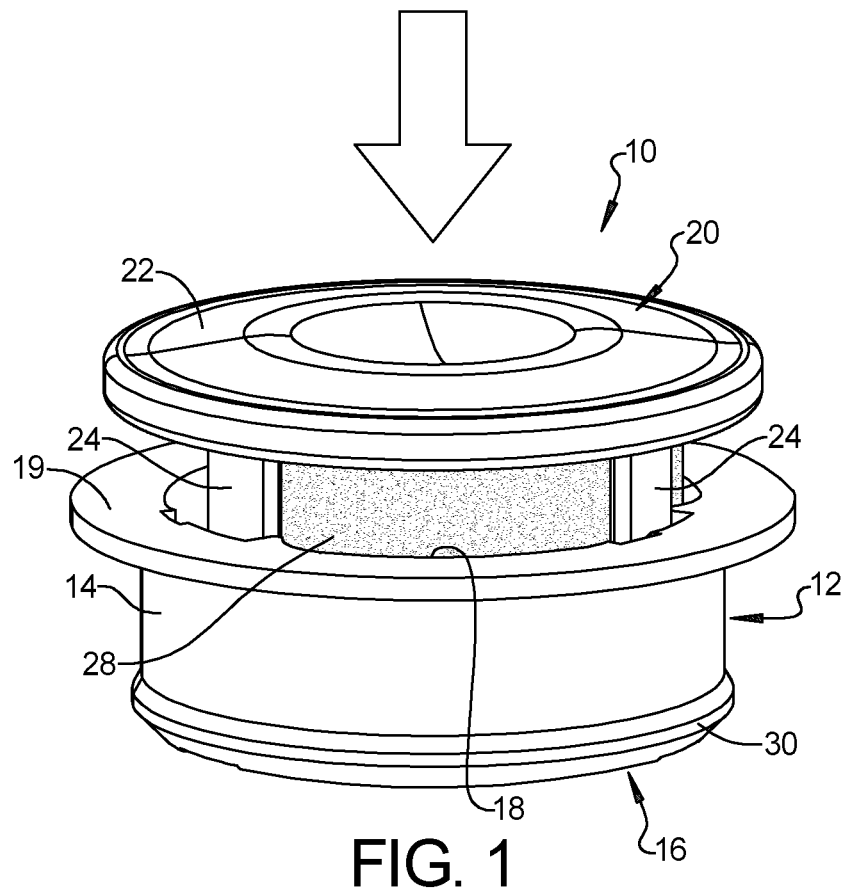
FIG. 1 is a top perspective view of a twist to lock tracheostoma valve and heat and moisture exchanger according to the principles of the present disclosure.
Figure 2:
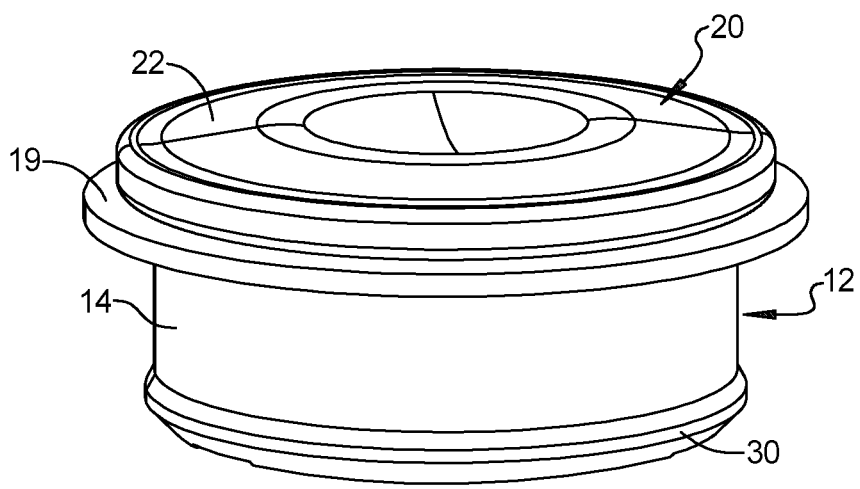
FIG. 2 is a top perspective view of the twist to lock adjustable tracheostoma valve and heat and moisture exchanger of FIG. 1 shown in a closed position.

With reference to FIG. 1, a twist to lock tracheostoma heat and moisture exchanger 10 is shown including a housing 12 that can have a cylindrical body 14 which, in use, includes an inboard opening 16 and an outboard opening 18 at opposite ends. The outboard opening is surrounded by a closure surface 19. A closure member 20 is supported by the housing 12. The closure member 20 includes a body 22 that can be disk shaped and a plurality of guide legs 24 extending from the body 22 and engaging a channel 25 (FIG. 4) in an inner surface 26 of the housing 12. A cylindrically shaped foam filter 28 is disposed within the housing 12 and underneath the body 22 of the closure member 20. As best shown in the partial cutaway view of FIG. 4, the housing 12 includes a retaining grid 29 in the inboard opening 16. The closure member 20 is movable between an open position wherein the body 22 is spaced from the housing 12, as shown in FIG. 1 and a closed position disposed against the closure surface 19 of the housing 12, as shown in FIG. 2. In the open position, the closure member 20 allows air to flow through the housing 12 as illustrated by arrow "A" during breathing and in the closed position, the closure member 20 prevent air from flowing through the housing 12, so as to allow speech by the wearer. The cylindrical body 14 of the housing 12 can include a retention flange 30 on an outer surface thereof for snap fit engagement with a tracheostoma base, not shown.

Figure 6:
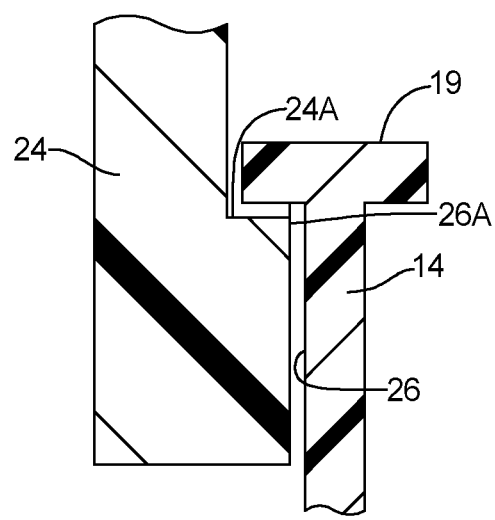
FIG. 6 is a cross-sectional view showing the retention feature of the closure member.

The housing 12 and the closure member 20 can each be made from a plastic material. With reference to FIG. 6, the closure member 20 can be retained in connection with the housing 12 by a lip 24A disposed on the end of the guide legs 24 that can engage a ledge 26A disposed on an inner surface 26 of the housing 12. The foam filter 28 acts as a spring for biasing the closure member 20 to an open position.

Figure 3:
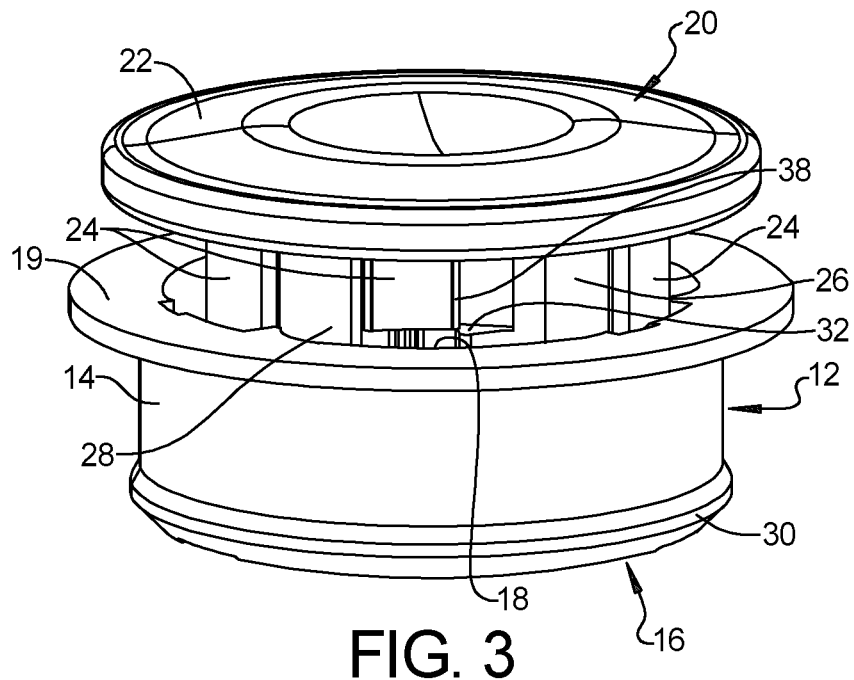
FIG. 3 is a top perspective view of the twist to lock adjustable tracheostoma valve and heat and moisture exchanger of FIG. 1 shown with the foam filter removed in order to better illustrate the twist to lock features.
Figure 4:
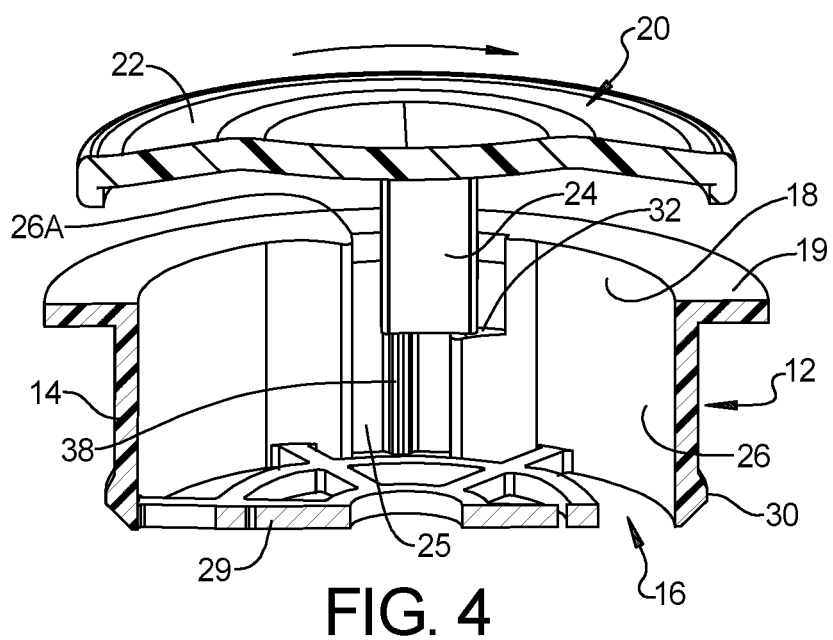
FIG. 4 is a partial cut-away top perspective view of the twist to lock adjustable tracheostoma valve and heat and moisture exchanger of FIG. 1 shown with the foam filter removed in order to better illustrate the twist to lock features.

With reference to FIGS. 3 and 4, the twist to lock tracheostoma heat and moisture exchanger 10 includes a locking mechanism (described herein) engageable to prevent movement of the closure member 20 to close a passage between the inboard and outboard openings 16, 18 and disengageable to allow movement of the closure member 20 to close the passage between the inboard and outboard openings 16, 18. The locking mechanism includes a plurality of ledges 32 disposed on the inner surface 26 of the housing. The closure member 20 can be positioned in a first position where the plurality of legs 24 extending from the body 22 of the closure member 20 can be out of alignment with the plurality of ledges 32 so that the closure member 20 is allowed to move to a closed position. The closure member 20 can be twisted to a locked position where the plurality of legs 24 extending from the body 22 of the closure member 20 are in alignment with the plurality of ledges 32 so that the closure member 20 is prevented from being moved to a closed position. Accordingly, the locking mechanism includes the plurality of ledges 32 and the plurality of legs 24 being engageable (FIG. 4) to prevent movement of the closure member 20 when the closure member is in a first rotatable position and being disengageable to allow movement of the closure member 20 to close the passage when the closure member 20 is in a second rotatable position (FIG. 3).

Figure 5:
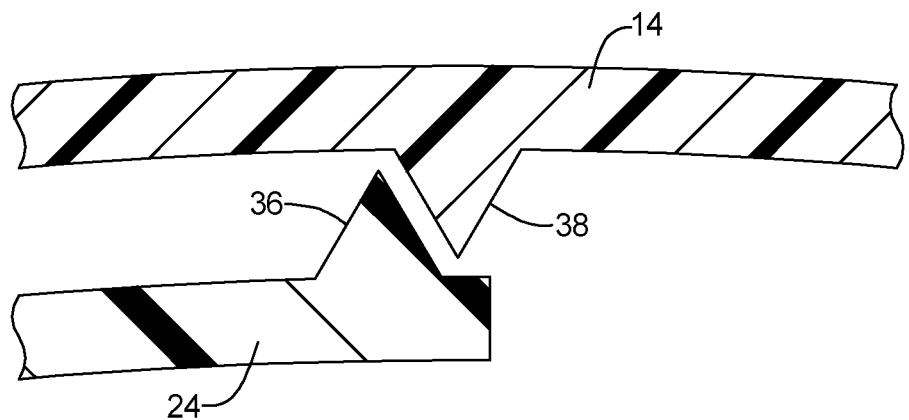
FIG. 5 is a cross-sectional view showing the detent features of the locking mechanism.

As shown in FIG. 5, the plurality of legs 24 each include a ramped detent 36 that engages corresponding ramped detents 38 on the inner surface 26 of the housing 12. The detents 36, 38 are movable relative to one another to rotatably retain the closure member 20 in either of the locked and unlocked positions. Accordingly, the closure member 20 can be rotated by hand to overcome the resistance provided by the detents 36, 38 for movement between the locked and unlocked positions. The twist to lock tracheostoma heat and moisture exchanger 10 allows a user to protect from accidental closure during activities when it would be preferred like sleeping and exercising.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A tracheostoma heat and moisture exchanging device, comprising:
    a housing having a first opening that is adapted to open to a tracheostoma and a second opening that opens to ambient;
    a foam filter disposed in the housing;
    a closure member mounted to the housing and adapted to close a passage extending through the housing;
    a locking mechanism engageable to prevent movement of the closure member to close the passage and disengageable to allow movement of the closure member to close the passage, wherein the locking mechanism includes a plurality of ledges disposed on a sidewall of the housing and a plurality of legs extending from the closure member wherein when the closure member is in a first rotatable position, the plurality of legs are each engageable with a respective one of the plurality of ledges to prevent movement of the closure member and when the closure member is in a second rotatable position the plurality of legs are each disengageable from the respective one of the plurality of ledges to allow movement of the closure member to close the passage; and
    a detent feature on each of the plurality of legs of the closure member for engaging a corresponding one of a plurality of detent features on the housing for retaining the closure member in either of the first position and the second position.

2. The tracheostoma heat and moisture exchanging device according to claim 1, wherein the housing includes a retention flange adapted for engaging a tracheostoma base.

3. The tracheostoma heat and moisture exchanging device according to claim 1, wherein the housing includes a retaining grid for retaining the foam filter in the housing.

4. A twist to lock tracheostoma heat and moisture exchanging device, comprising:
    a housing having a first opening that is adapted to open to a tracheostoma and a second opening that opens to ambient;
    a foam filter disposed in the housing;

a closure member including a body portion and a plurality of legs each engaged with a corresponding channel in an inner surface of the housing, the body portion being movable from an open position spaced from the housing to a closed position engaging the housing;

a locking mechanism including a plurality of ledges disposed in the inner surface of the housing that in a first position are each engageable with at least one of the legs of the closure member to prevent movement of the closure member to close the passage and wherein the closure member is rotatable relative to the housing to a second position wherein the plurality of legs are out of alignment with the plurality of ledges to allow movement of the closure member to the closed position; and a detent feature on each of the plurality of legs of the closure member for engaging a corresponding one of a plurality of detent features on the housing for retaining the closure member in either of the first position and the second position.

5. The twist to lock tracheostoma heat and moisture exchanging device according to claim 4, wherein the housing includes a retention flange adapted for engaging a tracheostoma base.

6. The twist to lock tracheostoma heat and moisture exchanging device according to claim 4, wherein the housing includes a retaining grid for retaining the foam filter in the housing.

7. The twist to lock tracheostoma heat and moisture exchanging device according to claim 4, wherein the plurality of legs each include a lip that engages a respective one of the plurality of ledges on the inner surface of the housing to retain the closure member to the housing.

* * * * *